(12) United States Patent
McIntyre et al.

(10) Patent No.: US 11,931,069 B2
(45) Date of Patent: Mar. 19, 2024

(54) ANCHORING SYSTEM AND METHOD FOR CRANIAL ACCESS

(71) Applicant: Rebound Therapeutics Corporation, Irvine, CA (US)

(72) Inventors: Todd D. McIntyre, Irvine, CA (US); Peter G. Davis, Irvine, CA (US); Ross Tsukashima, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 0 days.

(21) Appl. No.: 18/106,313

(22) Filed: Feb. 6, 2023

(65) Prior Publication Data

US 2023/0181216 A1 Jun. 15, 2023

Related U.S. Application Data

(63) Continuation of application No. 17/328,405, filed on May 24, 2021, now Pat. No. 11,571,241, which is a continuation of application No. 15/880,320, filed on Jan. 25, 2018, now Pat. No. 11,013,531.

(60) Provisional application No. 62/450,973, filed on Jan. 26, 2017.

(51) Int. Cl.
*A61B 17/34* (2006.01)
*A61B 17/02* (2006.01)
*A61B 17/16* (2006.01)
*A61B 17/17* (2006.01)
(Continued)

(52) U.S. Cl.
CPC ...... *A61B 17/3423* (2013.01); *A61B 17/3403* (2013.01); *A61B 17/3421* (2013.01); *A61B 17/0218* (2013.01); *A61B 2017/0225* (2013.01); *A61B 17/1695* (2013.01); *A61B 17/1739* (2013.01); *A61B 2017/3407* (2013.01); *A61B 2017/345* (2013.01); *A61B 2017/3458* (2013.01); *A61B 17/3462* (2013.01); *A61B 2017/3464* (2013.01); *A61B 2017/347* (2013.01); *A61B 2017/349* (2013.01);
(Continued)

(58) Field of Classification Search
CPC ............ A61B 17/1739; A61B 17/3462; A61B 17/3423; A61B 17/3421; A61B 17/3403; A61B 17/3417; A61B 17/0218; A61B 2017/3407; A61B 2017/345; A61B 2017/3458; A61B 2017/3464; A61B 2017/347; A61B 2017/0225; A61B 2017/349; A61B 2017/3492; A61B 2017/564; A61B 2090/103
USPC .......................................................... 600/204
See application file for complete search history.

(56) References Cited

U.S. PATENT DOCUMENTS 4,863,438 A * 9/1989 Gauderer .......... A61M 39/0247
604/105
5,000,745 A 3/1991 Guest et al.
(Continued)

*Primary Examiner* — Marcela I. Shirsat
(74) *Attorney, Agent, or Firm* — Crockett & Crockett, PC; K. David Crockett, Esq.

(57) ABSTRACT

An anchoring system for cannulas or tools to be inserted into a surgical workspace in the body, particularly the brain, of a patient. The system comprises a mounting ring which may be fixed to the skull to both secure the system to the skull and protect the skull opening from passage of cannulas and tools, a resilient clip with grasping jaws adapted to firmly grasp a cannula or tool, and a flexible membrane secured to the outer rim of the mounting ring and the clip.

8 Claims, 4 Drawing Sheets

(51) Int. Cl.
    *A61B 17/70*     (2006.01)
    *A61B 90/10*     (2016.01)

(52) U.S. Cl.
    CPC ... *A61B 2017/3492* (2013.01); *A61B 17/7055* (2013.01); *A61B 2090/103* (2016.02)

(56) References Cited

U.S. PATENT DOCUMENTS

| | | | |
|---|---|---|---|
| 5,026,352 A * | 6/1991 | Anderson | A61M 25/02 604/174 |
| 5,702,388 A | 12/1997 | Jackson et al. | |
| 5,800,451 A | 9/1998 | Buess et al. | |
| 7,316,699 B2 | 1/2008 | McFarlane | |
| RE44,790 E | 3/2014 | de la Torre et al. | |
| 8,845,655 B2 | 9/2014 | Henderson et al. | |
| 10,349,929 B2 | 7/2019 | Berti et al. | |
| 11,013,531 B2 * | 5/2021 | McIntyre | A61B 17/3421 |
| 2010/0057010 A1 | 3/2010 | Göransson | |
| 2014/0371537 A1 * | 12/2014 | Marczyk | A61B 17/3462 600/204 |
| 2017/0151032 A1 | 6/2017 | Loisel | |

\* cited by examiner

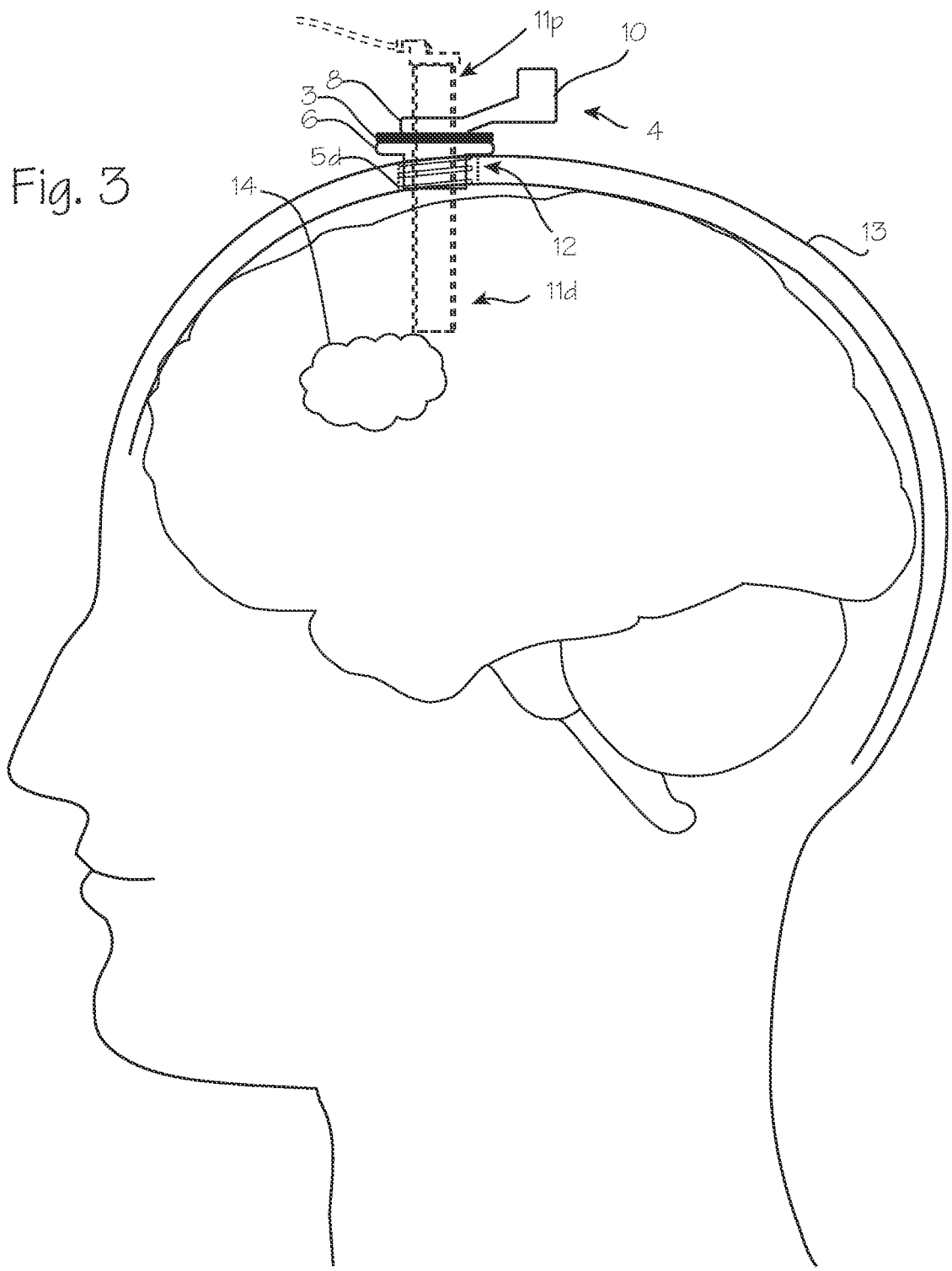

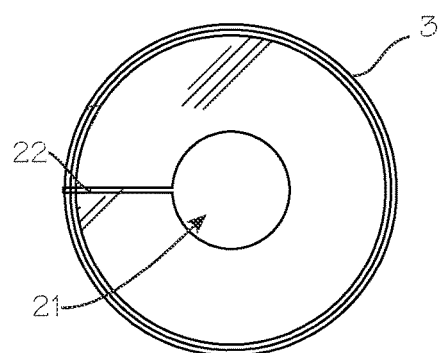
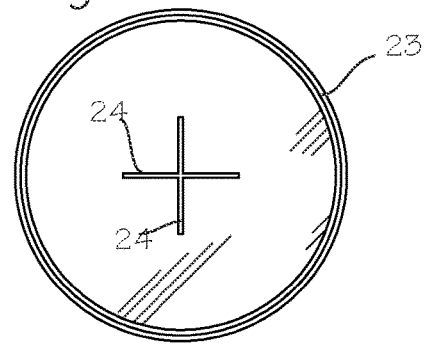
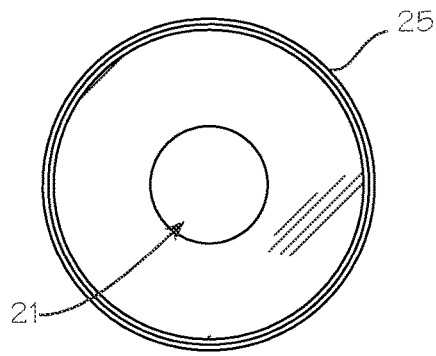
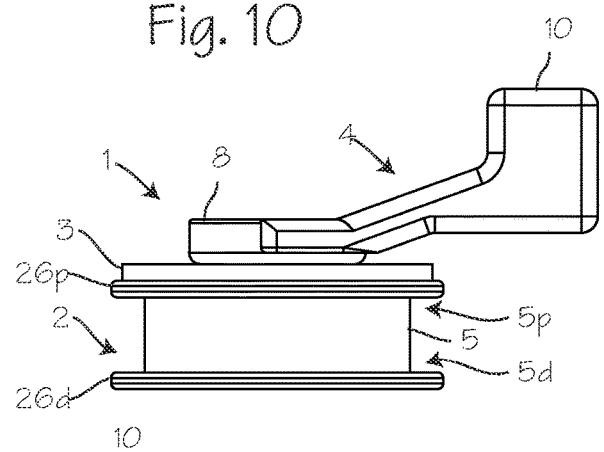
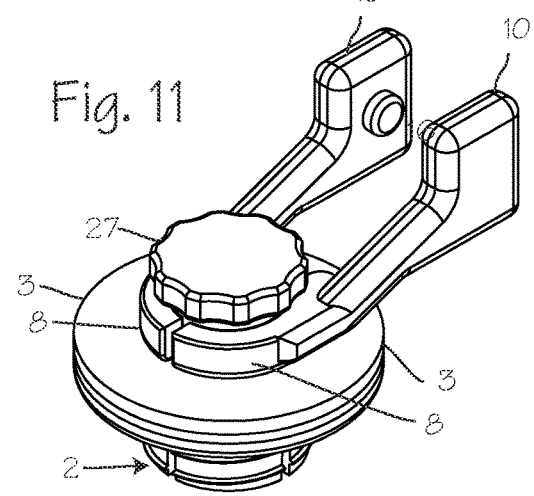

ANCHORING SYSTEM AND METHOD FOR CRANIAL ACCESS

This application is a continuation of U.S. application Ser. No. 17/328,405, filed May 24, 2021, now U.S. Pat. No. 11,571,241, which is a continuation of U.S. application Ser. No. 15/880,320, filed Jan. 25, 2018, now U.S. Pat. No. 11,013,531, which in turn claims priority to U.S. Provisional Application 62/450,973 filed Jan. 26, 2017.

FIELD OF THE INVENTIONS

The inventions described below relate to the field of minimally invasive brain surgery.

BACKGROUND OF THE INVENTIONS

Several disorders of the brain may be treated with minimally invasive tools and techniques. Blood masses resulting from hemorrhagic stroke, for example, may be removed by aspiration, with an aspiration tool inserted through a burr hole in the skull. Aneurysms and ruptured blood vessels can be treated with clips and/or cautery applied with devices inserted into the brain through a burr hole in the skull. Diagnosis of brain disorders may be accomplished with probes inserted through a hole in the skull. Other disorders can be treated with tools similarly inserted through a burr hole or craniotomy.

A few systems have been proposed for securing access to the brain through a burr hole. Some are quite complex, such as Henderson, et al., *Instrument Guide System*, U.S. Pat. No. 8,845,655 (Sep. 30, 2014). Henderson shows a surface mounted grommet/bushing/sleeve for installation in a hole in the skull. The grommet accommodates a guide tube that has a ball at the distal end which fits in a socket in the grommet, so that the guide tube can be tilted and rotated relative to the grommet. The grommet is screwed onto the skull to fix it. Henderson also refers to several patents with guide tube mounts that include tubular ball joints, or spherical ball and socket joints, to allow some angular play between the mount and the guide tube.

SUMMARY

The devices and methods described below provide for simple, secure, and flexible placement of a cannula or tool through an opening (a burr hole or craniotomy) in the skull of a patient. The device comprises a grommet which may be fixed to the skull to both secure the system to the skull and protect the skull opening from passage of cannulas and tools, a resilient clip with grasping jaws adapted to firmly grasp a cannula or tool, and a flexible membrane secured to the outer rim of the grommet and the clip. The clip holds a cannula or tool, which is inserted through the grommet, and prevents unintended inward or outward movement of the cannula or tool. The flexible membrane allows tilting of the cannula or tool, upon application of light force applied by a surgeon. The grommet may be secured to the skull with a friction fit into the skull opening, or may be secured with detents on resilient legs depending from the rim of the grommet, or may be secured to the skull by nailing, stapling or gluing it to the skull. In use, a surgeon will create a hole in the skull, insert the device into the hole such that the cylinder of the grommet lines the hole and the rim of the grommet rests on the superficial surface of the head, depending on the friction fit, detents or applying fasteners to secure the grommet to the skull, open the clip to its open configuration, pass a cannula or tool through the jaws of the clip and the opening in the grommet to a desired depth, and close the clip to secure the cannula or tool to the device. Thereafter, the surgeon may tilt the cannula or tool to obtain access to part of the brain within the arc of the cannula.

BRIEF DESCRIPTION OF THE DRAWINGS

FIGS. 3 and 4 illustrates use of the device to insert a cannula into the brain of a patient.

FIGS. 7, 8 and 9 illustrate variation of the membrane useful with the anchoring system.

FIGS. 10 and 11 illustrate additional features that may be provided in the anchoring system of the previous figures.

DETAILED DESCRIPTION OF THE INVENTIONS

Figure 1:
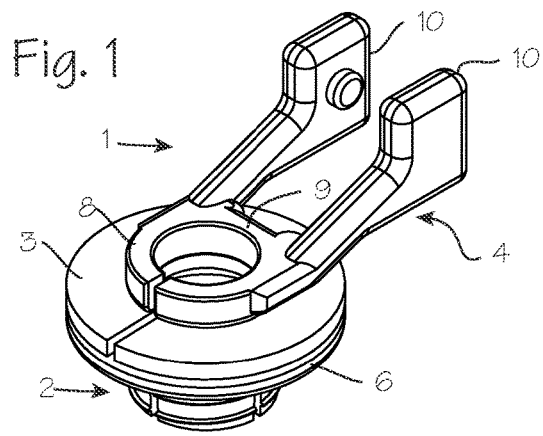
FIGS. 1 and 2 show the anchoring system for cranial access, with a grommet, flexible membrane, and clip.
Figure 2:
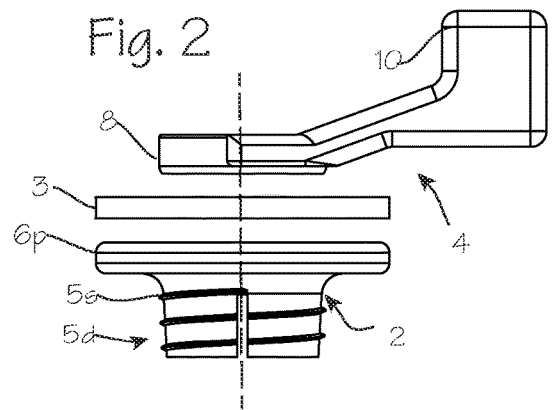

FIGS. 1 and 2 show the anchoring system for cranial access. The anchoring system 1 includes a grommet 2, flexible membrane 3, and clip 4.

The grommet, which is intended for placement into a hole in the skull of a patient to (1) protect the margins of the hole, including skin and bone, from degradation due to the passage of cannulas and tools and (2) secure the device to the skull. The grommet includes a tube 5, preferably a cylinder or cylindrical portion, which may include additional means which function to secure the grommet (screw threads 5s as illustrated, or detents, resilient protrusions, radially outwardly extending fingers or catches (a discontinuous annular snap joint) or any releasing or non-releasing snap-fit fittings such as a straight cantilevers or U-shaped cantilevers configured to engage the hole in the skull, for example). The cylindrical portion may also be formed as a spring, sized to closely fit a burr hole in the skull. The tube need not be continuous, and may have numerous slots. The tube is most conveniently a cylinder, to match the common form of burr holes, but may be provided in any cross-section to match the shape of a particular craniotomy or other aperture leading to a surgical site. The tubular portion is characterized, for convenience, by a distal end which is adapted to be inserted first into the hole, and a proximal end which is intended to be disposed near the surface of the skull, and a lumen extending through the tube, and defines a longitudinal axis of the grommet. The grommet also includes a rim or flange 6, disposed on the proximal end of the cylindrical portion, extending radially outwardly from the cylinder to provide a physical stop and facilitate attachment of the flexible membrane. Upon insertion, the grommet rests on the skull, with the rim or flange limiting inward motion of the grommet and the remainder of the device.

The flexible membrane, which secures the grommet to the clip, is preferably formed as an annulus (a flat ring, a flat disk with a hole in the center), like a washer, formed of a flexible material, such as silicone (in a flexible formulation) as shown in FIGS. 7 through 9, or several discrete straps extending from the cylinder proximal end to the clip. The hole 7 of the membrane is sized to accommodate the cannula or tool to be used in conjunction with the device. The grommet is secured, to the proximal end of the tube 5 (most conveniently fixed to the upper surface of the rim, though it may be fixed to the inner wall of the cylinder). The grommet is secured, at or near the inner edge of the membrane (the edge of the hole, or inner terminus of straps making up the membrane) to the clip 4.

The clip 4 comprises jaws 8, a hinge 9 joining the two jaws, and operating posts 10 fixed to the jaws and operable to be squeezed together to open the jaws. In the illustration, the jaws are secured, over a substantial portion of the lower surfaces of the jaws, to the membrane. The hinge may be provided in the form of a resilient joint joining two integrally formed jaw and post portions, or an actual hinge (with a hinge pin joining two discrete jaw and post parts), and the clip may be biased closed by the resilience of the resilient joint, or with a spring in an actual hinge or disposed between the posts. The membrane, when provided as a flat ring and fastened to much of the length of the jaws, may be split near the open end of the clip to facilitate opening.

The clip and its jaws are operable to grasp a cannula or tool 11. The jaws are sized to accommodate cannulas and tools that may be used for brain surgery, and the closing force of the clip is sufficient to prevent unwanted longitudinal movement (inward or outward movement along the axis of the devices). The closing force may be strong, so that the cannula or tool cannot be moved while the clip is closed upon the cannula or tool, or the closing force may be weak, so that the cannula or tool can be pushed longitudinally with some degree of force exceeding any expected accidental forces that might be applied. A layer of silicone or other soft or conformable elastomeric material may be disposed on the inner surface of each jaw to aid in securing the tool within the jaws.

Figure 4:
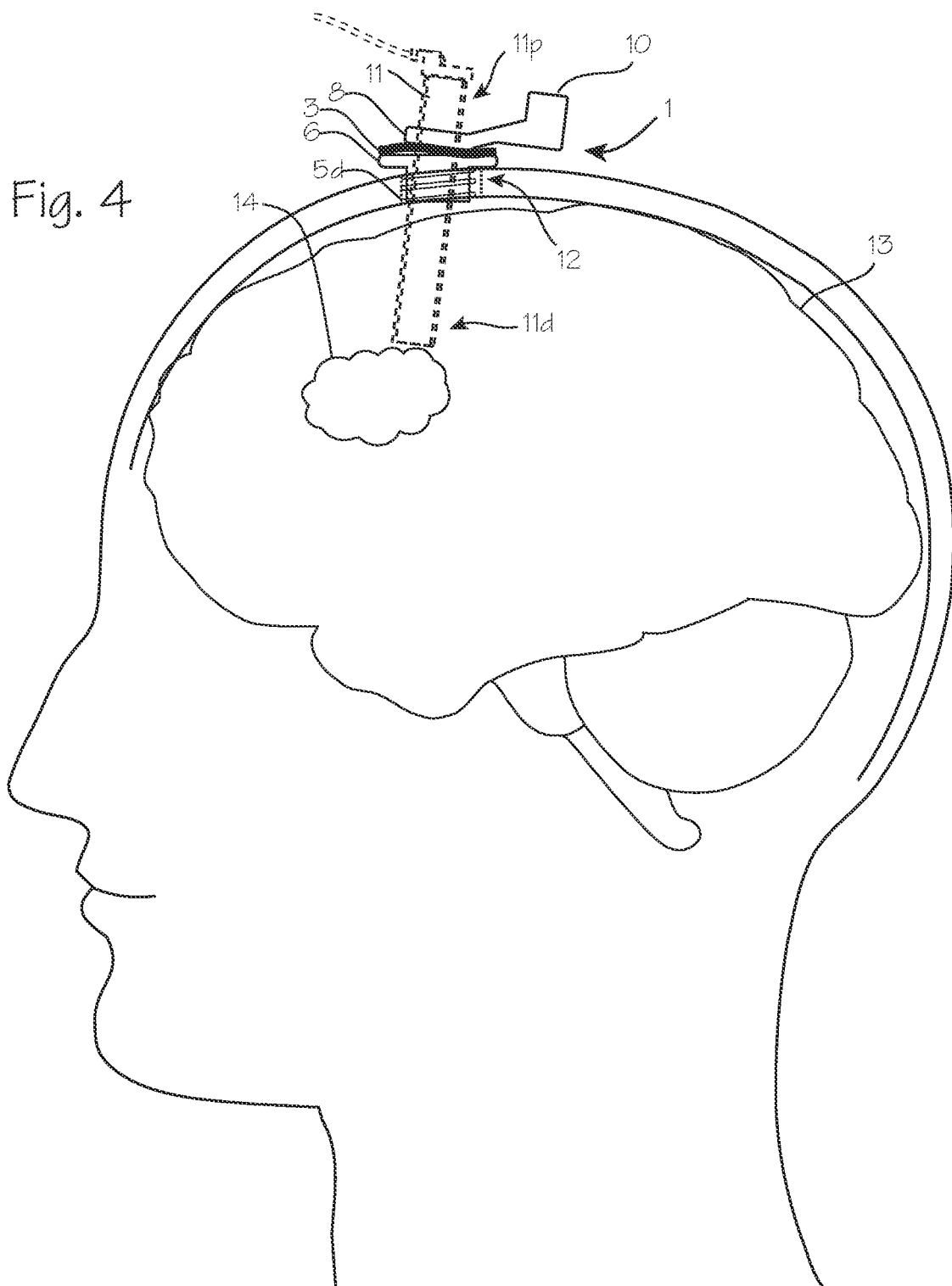

In use, the device is inserted into a hole in the skull of a patient to support a cannula or tool. As shown in FIG. 3, a surgeon inserts the distal end 5d of the cylinder 5 into a hole 12 in the skull 13 of a patient, so that the flange 6 is proximate the surface of the skull (and any intervening skin) and any securing means (detents, fingers, screw threads, etc.) engage the skull, or the surgeon nails, stitches, staples or glues the grommet to the skull. After the device is in place, the surgeon will squeeze (or otherwise manipulate) the operating posts 10 to open the jaws 8 of the device, and insert a cannula or tool 11, inserting the distal end 11d of the cannula or tool through the open jaws 8 and the membrane and into the brain to the desired extent, for example to a depth which allows treatment of a hemorrhagic blood mass 14. Next, the surgeon will release (or otherwise manipulate) the operating posts to allow the jaws to close on the cannula or tool. After placement, surgeon may tilt the cannula or tool to access areas of the brain that is not directly along the axis of the cylinder and flange, while the clip securely holds the cannula or tool and inhibits longitudinal movement (along the axis of cylinder and flange) of the cannula or tool. As shown in FIG. 4, the cannula or tool 11 may tilt when pushed by the surgeon, and the membrane 3 will flex to allow the cannula to tilt while the jaws inhibit inward movement of the cannula or tool. When the surgeon is finished with the procedure, the surgeon will remove the cannula or tool, and pull the device from the hole.

Figure 6:
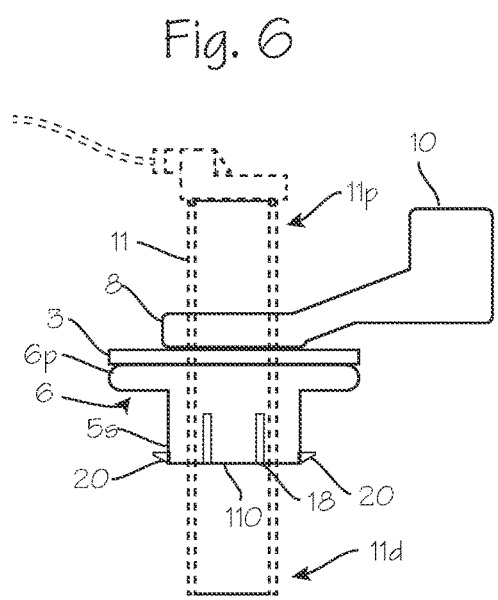
FIGS. 5 and 6 illustrate the device with various means for fastening the grommet to the brain.
Figure 5:
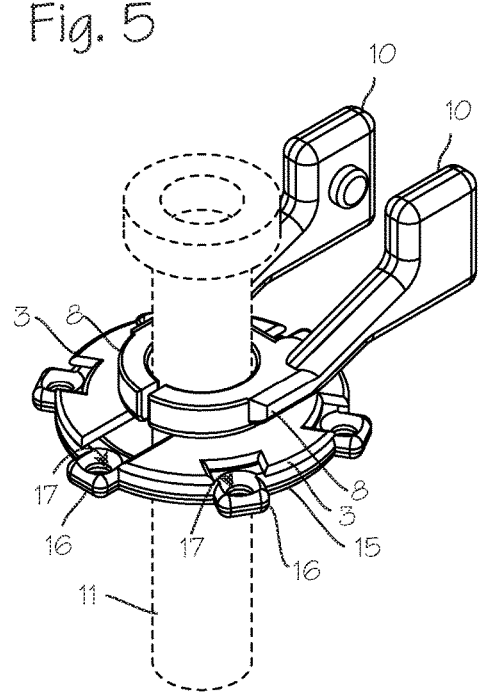

FIG. 5 illustrates an alternate means for securing the device to the skull. The device of FIG. 5 includes a mounting ring 15 (in place of the grommet 2) with several radially extending projections 16 with guide holes 17 which may accommodate nails. To secure this device to the skull, the surgeon will insert nails in to the guide holes and drive the nails into the skull, or stitch or staple the projection to the skin around the skull opening. FIG. 6 also illustrates an alternate means for securing the device to the skull. The device of FIG. 6 includes a grommet 2 with a flange 6 and cylinder 5. The cylinder is slotted, with several longitudinally extending slots 18 to form several depending legs 19, each with a radially extending finger 20. The legs are resilient, and will flex inwardly upon insertion of the cylinder through the hole in the skull, thus allowing fingers to pass through the hole. The legs resiliently expand when the fingers pass the skull and enter the brain, to hold the grommet in place. Thus, the means for securing the grommet may take several forms.

Material used for the flange and grasper may comprise metals including spring steel, abs plastic, acrylic, nylon, PPS or other suitable biocompatible material with sufficient rigidity to serve as a grommet, or the grasping jaws and resilient living hinge. Regardless of the material chosen for the grommet or jaws, the structure should be rigid in comparison to the membrane, such that the membrane is deformed during the use of the device by the opening force of the jaws, and the manipulation of a cannula held in the device will not result in deformation of the grommet, or extraction of the grommet, before the membrane is deformed sufficiently to allow a range of movement for the cannula.

Materials used for the flexible membrane may comprise a flexible polymer such as silicone, low density polyethylene, rubber, etc. The stiffness of the membrane may be dependent on the material chosen, the diameter of the membrane, and thickness of the membrane, so the membrane should be configured such that it is significantly more flexible than the grommet and jaws, such that the (1) opening, squeezing force applied to the operating post 10 results in opening of the jaws and resilient deformation of the membrane, rather than deformation of the posts, and (2) radial forces applied to the proximal end of a cannula held in the jaws results in tilting of the cannula relative to the grommet (within the radius of the grommet), and deformation of the membrane, rather than dislodgement of the grommet from the burr hole in which it is temporarily fixed.

FIGS. 7, 8 and 9 illustrate variations of the membrane useful with the anchoring system. FIG. 7 shows the membrane used in device of FIG. 1, comprising a membrane 3 of flexible material with central aperture 21 a small slit 22 extending radially and communicating from the aperture in the center of the annulus to the outer edge of the annulus. As shown, the membrane has a circular aperture and a circular outer perimeter, but these shapes may be varied to suit various tools or manufacturing techniques. FIG. 8 shows a membrane 23 with several centrally located slits 24, radiating radially from the center of the membrane without extending to the outer perimeter of the membrane. FIG. 9 shows a membrane 25 with a central aperture 21, but without the radial slit shown in the membrane of FIG. 7, establishing an uninterrupted annular membrane. The slit of FIG. 7 facilitates opening of the jaws which are fixed to the membrane, while the configurations of FIGS. 8 and 9 will maintain a seal around a cannula or tool extending through the membrane.

FIGS. 10 and 11 illustrate additional features that may be provided in the anchoring system of the previous figures. The anchoring system 1 of FIG. 10 includes, in addition to the grommet 2 (including the tube 5), the membrane 3 and the clip 4 (with the jaws 8 and operating posts 10), a skin seal 26p on the proximal end 5p of the grommet tube and/or a skin seal 26d on the distal end 5d of the grommet tube 5. Each skin seal may comprise a very soft and compliant ring surrounding the tube 5, compressible against the body tissue surface (external or internal) so as to limit leakage of fluids from the surgical workspace around the grommet. The distally located skin seal 26d may serve as the means for securing the grommet to the skull, and may be described as a continuous annular snap-fit fitting interoperable with the hole in the skull to secure the grommet tube to the skull. The anchoring system 1 of FIG. 11 includes, in addition to the grommet 2, the membrane 3 and the clip 4, a plug or cap 27 which may be inserted into the jaws 8 and aperture of the membrane to seal the surgical space so that, for example, the anchoring system may be left in place for an extended period, either intra-operative of per-operative, to allow for repeated access to the surgical site. The plug is configured (sized and shaped relative to the jaws and aperture) for insertion into the grasping jaws and aperture of the membrane to occlude the aperture and thereby seal the surgical space when the device is installed in a patient.

An embodiment which includes the plug of FIG. 11 may be used in procedures that require repeated access, such as drainage of excess fluid in the brain. The anchoring system can be installed to support an initial treatment of ICH, for example, and then left in place to support drainage or aspiration over the course of several days, and removed thereafter. While the anchoring system is left in place, the plug may be installed to close off the surgical work space from the environment.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A device for anchoring a cannula or tool to a surgical portal of a patient, said device comprising:
    a mounting ring having a lumen and defining a longitudinal axis of the device, said mounting ring not comprising a depending tube;
    a flexible membrane having a perimeter and an aperture disposed within the membrane, said flexible membrane secured to the mounting ring on a first side of the flexible membrane, with the aperture of the membrane disposed over the lumen of the mounting ring;
    a clip having grasping jaws and a hinged connection between the grasping jaws, and operating posts connected to the grasping jaws, said grasping jaws fixed to the flexible membrane, on a second side of the flexible membrane opposite the first side of the membrane; wherein
    the clip and flexible membrane are aligned over the mounting ring such that the grasping jaws open over the hole in the membrane and the lumen of the mounting ring; and wherein
    the aperture of the membrane defines an inner edge of the membrane, and the clip is secured to the inner edge of the membrane, and thereby secured to the mounting ring.

2. The device of claim 1, wherein the membrane comprises silicone.

3. The device of claim 1, further comprising:
    means for securing the mounting ring to a hole in the patient.

4. The device of claim 3, wherein the means for securing the mounting ring comprise:
    a plurality projections extending radially from the mounting ring, with each of the plurality projections having a guide holes configured to accommodate nails, stitches or staples for securing the mounting ring on the patient.

5. The device of claim 1 further comprising:
    a plug for occluding the mounting ring, said plug configured for insertion into the grasping jaws and hole of the membrane to seal a surgical space when the device is installed in a patient.

6. The device of claim 1 further comprising:
    a layer of conformable elastomeric material disposed on the inner surface of each jaw.

7. The device of claim 1 wherein:
    the hinged connection joins the jaws together.

8. The device of claim 1 wherein:
    the hinged connection joins the jaws together such that the operating posts are operable to open the jaws when the operating posts are squeezed together.

* * * * *